United States Patent [19]

Helioff et al.

[11] Patent Number: 4,957,731

[45] Date of Patent: Sep. 18, 1990

[54] HAIR PROCESSING ADDITIVES

[75] Inventors: Michael W. Helioff, Westfield; Carmen D. Bires, Long Valley; Robert B. Login, Oakland, all of N.J.

[73] Assignee: GAF Chemicals Corporation, Wayne, N.Y.

[21] Appl. No.: 340,194

[22] Filed: Apr. 19, 1989

Related U.S. Application Data

[63] Continuation-in-part of Ser. No. 188,522, Apr. 29, 1988, Pat. No. 4,885,158, Continuation-in-part of Ser. No. 91,149, Aug. 28, 1987, Pat. No. 4,837,013, which is a continuation-in-part of Ser. No. 922,923, Oct. 24, 1986, Pat. No. 4,732,990, Continuation-in-part of Ser. No. 91,010, Aug. 28, 1987, Pat. No. 4,883,655, which is a continuation-in-part of Ser. No. 922,923, Oct. 24, 1986, Pat. No. 4,732,990, Continuation-in-part of Ser. No. 91,008, Aug. 28, 1987, Pat. No. 4,830,850, which is a continuation-in-part of Ser. No. 922,923, Oct. 24, 1986, Pat. No. 4,732,990, Continuation-in-part of Ser. No. 67,195, Jun. 29, 1987, Pat. No. 4,834,970, which is a continuation-in-part of Ser. No. 922,923, Oct. 24, 1986, Pat. No. 4,732,990, Continuation-in-part of Ser. No. 60,285, Jun. 10, 1987, Pat. No. 4,871,535, which is a continuation-in-part of Ser. No. 922,923, Oct. 24, 1986, Pat. No. 4,732,990, Continuation-in-part of Ser. No. 60,284, Jun. 10, 1987, Pat. No. 4,834,767, which is a continuation-in-part of Ser. No. 922,923, Oct. 24, 1986, Pat. No. 4,732,990.

[51] Int. Cl.$^5$ .................... A61K 7/075; A61K 7/135; A61K 7/13; A61K 7/09

[52] U.S. Cl. ......................................... 424/62; 424/70; 424/71; 424/72; 8/405; 8/406; 252/DIG. 13

[58] Field of Search ................. 424/70, 71, 72, 62; 8/405, 406; 252/DIG. 13

[56] References Cited

U.S. PATENT DOCUMENTS

| | | | |
|---|---|---|---|
| 4,532,127 | 7/1985 | Feinland | 424/62 |
| 4,579,732 | 4/1986 | Grollier | 424/71 |
| 4,885,158 | 12/1989 | Tracy | 424/69 |

Primary Examiner—Merrell C. Cashion, Jr.
Assistant Examiner—Susan S. Rucker
Attorney, Agent, or Firm—Marilyn J. Maue; Joshua J. Ward

[57] ABSTRACT

A composition comprising an aqueous hair coloring, bleaching, reducing, oxidizing or permanent structure altering formulation and a conditioning amount of a quaternized compound having the formula

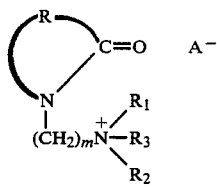

wherein m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkyleneoxyalkyl, alkyleneoxyalkenyl, alkoxy, hydroxyalkyl, aryl, aralkyl, alkaryl, alkyleneamidoalkyl, alkylenecarbamoylalkyl, aryleneamidoalkyl and arylenecarbamoylalkyl radicals, and $R_2$ and $R_3$, together with the quaternized nitrogen atom can form a heterocyclic radical containing from 1 to 2 heteroatoms selected from the group of nitrogen, sulfur and oxygen, in which case $R_1$ can represent a double bond in the heterocyclic structure or can be any of the aforementioned groups for $R_1$, $R_2$ and $R_3$; said groups $R_1$, $R_2$ and $R_3$ each having up to 30 carbon atoms and at least one of $R_1$, $R_2$ and $R_3$ being a radical having from 8 to 30 carbon atoms when $R_2$ and $R_3$ are not part of a heterocyclic moiety; and $A^-$ is an anion derived from an oxylated sulfur compound, having the formula:

$$R'SO_3^-$$

wherein R' is alkyl, alkoxy, phenyl, phenoxy, alkylenephenyl, alkylenephenoxy, phenylenealkyl or phenyleneoxyalkyl and wherein the alkyl moieties of said R' groups contain from 1 to 20 carbon atoms and said R' groups are optionally alkoxylated with from 1 to 20 units of ethyleneoxide and/or propylene oxide.

14 Claims, No Drawings

HAIR PROCESSING ADDITIVES (1) This application is a continuation in part of 07/188,522, Apr. 29, 1988, U.S. Pat. No. 4,885,158.

(2) This application is a continuation in part of 07/091,149, Aug. 28, 1987, U.S. Pat. No. 4,837,013, which is a continuation in part of 06/922,923, Oct. 24, 1986, U.S. Pat. No. 4,732,990.

(3) This application is a continuation in part of 07/091,010, Aug. 28, 1987, U.S. Pat. No. 4,883,655, which is a continuation in part of 06/922,923, Oct. 24, 1986, U.S. Pat. No. 4,732,990.

(4) This application is a continuation in part of 07/091,008, Aug. 28, 1987, U.S. Pat. No. 4,830,850, which is a continuation in part of 06/922,923, Oct. 24, 1986, U.S. Pat. No. 4,732,990.

(5) This application is a continuation in part of 07/067,195, June 29, 1987, U.S. Pat. No. 4,834,970, which is a continuation in part of 06/922,923, Oct. 24, 1986, U.S. Pat. No. 4,732,990.

(6) This application is a continuation in part of 07/060,285, June 10, 1987, U.S. Pat. No. 4,871,535, which is a continuation in part of 06/922,923, Oct. 24, 1986, U.S. Pat. No. 4,732,990.

(7) This application is a continuation in part of 07/060,284, June 10, 1987, U.S. Pat. No. 4,834,767, which is a continuation in part of 06/922,923, Oct. 24, 1986, U.S. Pat. No. 4,732,990.

In one aspect the invention relates to an aqueous composition containing a softening and penetrating agent for keratin protein reduction which agent enhances cleavage of the disulfide bond of the hair cystine residue to form the corresponding cysteine residue in a process for altering the structure and/or configuration of hair as in straightening or permanent waving. In another aspect, the invention relates to an agent which promotes hard water solubility of a neutralizing lotion employed in a reducing process for altering the structure and/or configuration of hair. In still another aspect, the invention relates to an aqueous composition containing a hair conditioning amount of a keratin penetrating agent for altering the color of hair as in tinting, dyeing or bleaching or for improving softness and combability in a hair conditioning preparation.

BACKGROUND OF THE INVENTION

The activity or effectiveness of hair shaping preparations is based mainly on the inclusion therein of an agent for softening and relaxing the keratin protein present in hair by reducing the disulfide linkages of keratin. The hair fiber is wound on rods to achieve the desired waving effect or manipulated into a straightened condition and allowed to remain wetted with the reducing lotion for a desired period, after which the reducing lotion is rinsed off and finally oxidized with a neutralizing solution or air oxidized.

Basically, hair is softened and swelled by rupture of disulfide bonds present in the cystine component of keratin by the use of a mild alkaline reducing agent. Cleavage of at least some of the disulfide bonding to form the corresponding cysteine residue is necessary to allow for molecular rearrangement which takes place during the hair fiber molding operation. The reductive fission of hair disulfides qenerally causes reddening of the scalp area and damage to the hair fiber, particularly hair which has been bleached, tinted or otherwise damaged. Current hair structure altering lotions which provide relaxation of imposed stress include aqueous solutions of alkaline mercapto compounds, sulfites or bisulfites at a pH of between 7 and 9.5. In order to obtain a permanent effect, particularly in hair straightening, it is often necessary to introduce the active agent in relatively high concentration with the result that the reducing lotion is provided at almost the limit of its physiological compatability or tolerability.

Damage to hair is increased where heat waving, as opposed to cold waving, is employed. Of the reducing agents currently in use, the thioglycolates or thioglycolic acid, dithioglycolic acid and mercapto compounds such as ammonium thioglycolate, glyceryl, monothioglycolate, mercapto propionic acid and mercapto ethyl amine are most often employed in professional waving or hair straightening. Alkaline sulfites and bisulfites are generally reserved for home permanent use. In addition to the reducing agent, alkalis having a dissociation constant less than $5 \times 10^{-3}$, are also used to facilitate diffusion through the hair. These promotors include ammonia, ammonium hydroxide, ethanol amine, diisopropanol amine, glycine, and lysine.

In an attempt to minimize these harmful effects polymeric quaternized amines have been developed as reducing agent supports, e.g. see U.S. Pat. No. 4,579,732. These basic compounds have not been found to be completely satisfactory for the reason that they react with anionic components which are often present in hair structure altering compositions. Additionally the terminal amino groups react with hydrogen peroxide to form nitrogen oxides, thus increasing the effective amounts of peroxide which must be employed in fixing solutions. Since peroxides are known to have a hair drying effect, it is desirable to maintain the peroxide at a minimum level. In addition the large molecular size of these polymeric products prevents their penetration into the hair fiber and instead forms a coating over the hair which is subject to tack under conditions of high humidity. Further, many reducing lotions produce a disagreeable odor during reduction of the cystine molecule which the polymeric amines are unable to overcome. Finally, the relatively high viscosity of these quaternized polymers together with the normal variations in molecular weight in the polymer chains in the product lead to formulation problems in reproducability of product quality and in storage of the product over extended periods.

All of the commercial reducing lotions cause some degree of hair damage depending on the tightness and thickness of the curl, the temperature of processing, the concentration of the alkaline reducing agent and the condition of the hair. Accordingly, the art continues to seek means and possibilities whereby to provide for the aforesaid waving and straightening lotions, compositions which are less damaging to the skin and hair and which contain stable components simple to incorporate into the standard reducing lotions currently in use so as to provide the same or more effective results for heat or cold permanent waving and hair straightening. One method for the realization of these objects can be achieved by promoting penetration of the reducing lotion and providing absorption at a faster rate so that the time hair fiber is exposed to chemical action is reduced.

Secondary aims for permanent waving compositions include masking the thiol odor of the reducing lotion, providing non-degradable compounds which may be easily and reproduceably formulated and minimizing skin irritation caused by routine exposure of professional hair dressers or erythema on the scalp and neck of the subject undergoing treatment.

In regard to hair color, the main coloring component is a dark pigment, melanin, which occurs as granules embedded in the hair cortex. The aim of bleaching is to decolorize selectively the natural pigments or applied pigments in the hair with minimal damage to the hair matrix. When hair is bleached, the color changes to lighter and lighter shades depending upon the amount of melanin granules dissolved and removed from the hair fiber. Hydrogen peroxide is the leading solvent for melanin used in the bleaching process; however, along with melanin removal, the peroxide reacts with keratin to cause loss of tensile properties and damage to the hair. More specifically, bleaching occurs in two steps: (1) initial solubilization of the color granules, and (2) decolorization of the dark brown solubilized pigment. The reaction between melano-protein and hydrogen peroxide is confined mainly to the protein-combined cystine residues which are subsequently converted to combined cysteic acid. The solubilization of the melanin granules is connected with the splitting of the disulfide bridges in the melano protein and it is likely that the disulfide bridge may be the stabilizing factor in melanin, as it is in keratins.

The bleaching process can be halted at any point or can be permitted to continue to a light blonde or platinum shade. The latter provides a good background for a variety of tints which can be obtained by a subsequent coloring step. Such bleaching and coloring combination is known as a double process coloring and causes hair damage by promoting porosity, brittleness, loss of tensile strength and dryness.

Permanent hair colorants involve the use of oxidation dye intermediates which are colorless substances but which, when mixed with oxidizing agents just prior to use, produce color by a process of oxidative condensation. More specifically, the intermediates, in the presence of an oxidant, couple with another oxidation dye intermediate molecule to form a large fused ring color compound within the hair fiber. Since the fused ring product is too large to penetrate the hair fiber, it is essential that good penetration is achieved by the precursor intermediate. The oxidation dye process engenders many changes in the chemical and cosmetic characteristics of the hair which are undesirable. Specifically, the effect of alkali swelling of the hair fiber leads to loss of tensile strength, flexibility and promotes a porous, dry appearance. Additionally, the oxidation dye intermediates often cause skin sensitivity and reddening. Still further, the color imparted on processed hair is often non-uniform since the preprocessed sections, have higher porosity and absorb the intermediate at a faster rate than virgin growth which is more resistant to absorption.

Certain quaternized amine compounds and polymeric amines as disclosed in U.S. Pat. Nos. 4,532,127 and 4,579,732 have been developed to overcome some of the above problems. However these basic compounds have not been found to be completely satisfactory since they react with anionic components which are commonly present in hair coloring or bleaching compositions. This reactivity causes undesirable alterations in the shade desired. Additionally the amino groups react with hydrogen peroxide to form nitrogen oxides, thus increasing the effective amount of peroxide which must be employed in bleaching compositions. Since peroxides are known to have a drying effect on hair, it is desirable to use as little as possible to obtain the desired effect. Further the relatively high viscosity of the polymeric compounds together with the normal variation in molecular weight of the polymer chains in the product lead to formulation problems in reproducibility of product quality and in storage of the product over extended periods. In addition the large molecular size of the polymeric products prevents their penetration into the hair fiber and instead forms a coating over the hair, which may develop tack under conditions of high humidity. Finally, many hair dye and bleaching compositions produce a disagreeable odor which the prior quaternized amino compounds do not mask.

Accordingly, it is an object of this invention to achieve the various aims enumerated above by a simple and commercially feasible process involving the addition of the compound of the present invention as a component in standard hair processing or treating formulations, including structure altering, color altering, shampooing and conditioning formulations, used both professionally and at home.

Another object of the invention is to provide an additive to hair reducing lotions which promotes a higher degree of curl in a shorter period of time.

Another object of the invention is to provide an additive which actually conditions the hair undergoing a color altering or restructuring treatment or other cosmetic treatments.

Another object is to provide a compound which, when added to a hair coloring, hair bleaching, hair waving or straightening lotion, increases the penetration rate of the lotion to minimize run-off and dripping.

Yet another object is to provide a long lasting processing affect that moisturizes and protects the hair fiber so as to give the processed hair a silky softness.

Still another object is to provide an additive which improves hard water solubility of components in various hair processing lotions.

Still another object is to provide a non-polymeric compound of reproduceable composition which is substantially non-reactive with respect to anionic components and hydrogen peroxide and which is stable under conditions of high humidity.

Yet another object of this invention to overcome or minimize the deficiencies of prior hair preparations by providing a chemically stable additive which obviates skin sensitization, conditions the hair during processing, aids in the penetration of dye intermediate without undue alkaline swelling of the hair fiber, provides complexing sites on which the colorant can form, minimizes the period of hair exposure to chemical solutions, provides a more uniform distribution of color to processed hair by promoting penetration in portions of new hair growth, preserves the tensile properties of bleached or dyed hair, improves curl retention and successfully masks undesirable thiol odors.

These and other objects of the invention will become apparent from the following description and disclosure.

THE INVENTION

In accordance with the present invention there is provided a quaternized amino lactam which is incorporated into a hair processing formulation in an effective conditioning amount, such as for example, in a concentration of between about 0.01 to about 7 wt. %, preferably between about 0.05 and about 5 wt. % based on total weight of the respective treating lotions. The amino lactams of the present invention are defined by the structure

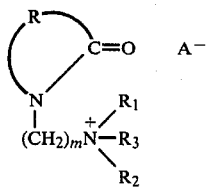

wherein m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkyleneoxyalkyl, alkyleneoxyalkenyl, alkoxy, hydroxyalkyl, aryl, aralkyl, alkaryl, alkyleneamidoalkyl, alkylenecarbamoylalkyl, aryleneamidoalkyl and arylenecarbamoylalkyl radicals, and $R_2$ and $R_3$, together with the quaternized nitrogen atom can form a heterocyclic radical containing from 1 to 2 heteroatoms selected from the group of nitrogen, sulfur and oxygen, in which case $R_1$ can represent a double bond in the heterocyclic structure or can be any of the aforementioned groups for $R_1$, $R_2$ and $R_3$; said groups $R_1$, $R_2$ and $R_3$ each having up to 30 carbon atoms and at least one of $R_1$, $R_2$ and $R_3$ being a radical having from 8 to 30 carbon atoms when $R_2$ and $R_3$ are not part of a heterocyclic moiety; and $A^-$ is an anion derived from an oxylated sulfur compound, having the formula:

$$R'SO_3^-$$

wherein R' is alkyl, alkoxy, phenyl, phenoxy, alkylenephenyl, alkylenephenoxy, phenylenealkyl or phenyleneoxyalkyl and wherein the alkyl moieties of said R' groups contain from 1 to 20 carbon atoms and said R' groups are optionally alkoxylated with from 1 to 20 units of ethyleneoxide and/or propylene oxide.

Representative of the above anions, $R'SO_3^-$, are methyl sulfate, methyl sulfonate, ethyl sulfate, ethyl sulfonate, (8)ethoxylated methyl sulfate, (6)propoxylated methyl sulfate, (10)propoxylated ethyl sulfate, (4)ethoxylated ethyl sulfonate, lauryl sulfate, (3)ethoxylated lauryl sulfate, lauryl sulfonate, decyl sulfate, dodecyl sulfonate, octadecyl sulfate, octadecyl sulfonate, tetradecyl sulfate, tetradecyl sulfonate, (4)ethoxylated lauryl sulfonate, $C_{12}$ to $C_{20}$ α-olefin sulfates and sulfonates or mixtures thereof, xylene sulfate, xylene sulfonate, benzene sulfate, benzene sulfonate, ethylphenyl sulfate, dodecylphenyl sulfonate, toluene sulfate, toluene sulfonate, etc. and mixtures thereof.

Of these, the lactams having the formula

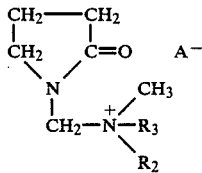

are preferred and include those pyrrolidones wherein at least one of $R_2$ and $R_3$ is octadecyl, hexadecyl, tetradecyl, hydrogenated tallow or coco and wherein the other of $R_2$ and $R_3$ is methyl or the same as $R_3$. Most preferred are the pyrrolidones wherein $R_3$ is hexadecyl or octadecyl, which are employed in the above defined formulations or lotions at a concentration of between about 0.75 and about 5.00 wt. %. Reducing lotions are generally benefited with between about 0.75 and about 1.50 wt. %.

The terms "formulation", "preparation" or "lotion", as used herein, include a cream, a gel, a paste, an emulsion or a watery liquid.

The present lactams can be used individually or in admixtures and can be employed to replace any of the promoters commonly present in commercial hair lotions including heat or cold permanent waving preparations utilizing water wrap or lotion wrap procedures, hair bleaching or oxidizing dye intermediate formulations, compositions containing an oxidation dye intermediate including a permanent shampoo tint, a permanent hair dye, hair bleach, hair blanch or hair dye removal preparation for home or professional use, or commercial hair conditioning and/or shampooing formulations. Alternatively, the present preparations may be made up using the individual components normally included in such preparations currently marketed in the same or different proportions or mixtures wherein the lactams of this invention are added to improve properties and minimize hair damage.

Particular structure or color altering formulations and shampoos included herein are described in detail in copending U.S. patent applications Ser. Nos. 060,284 and 060,285 now U.S. Pat. Nos. 4,834,767 and 4,871,535 respectively. These patent applications additionally disclose the benefits of halogen salt quaternized lactam additives all of which benefits apply, in an even higher degree, to the present lactams. Accordingly, the entire teaching of said patent applications are incorporated herein by reference.

In general, the compounds of the present invention can be prepared by several different methods. For example, sulfates and sulfonates corresponding to the above anions may be ion exchanged with the halides of the compounds disclosed in co-pending patent applications Ser. No. 922,923, filed Oct. 24, 1986 now U.S. Pat. No. 4,732,990; Ser. No. 067,195, filed June 29, 1987 now U.S. Pat. No. 4,834,970; and Ser. Nos. 091,010; 091,008 and 091,149 all filed Aug. 28, 1987 now U.S. Pat. Nos. 4,883,655, 4,830,850 and 4,837,013 respectively and applications Ser. Nos. 060,284 and 060,285, now U.S. Pat. Nos. 4,834,767 and 4,871,535 respectively (supra) each incorporated herein by reference. Said halide compounds are defined by the general formula

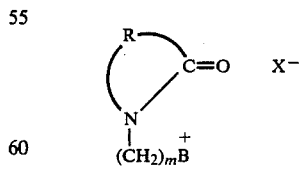

wherein $X^-$ is a chloride, bromide, or iodide anion; m is an integer having a value of from 1 to 4; R is linear alkylene having from 3 to 8 carbon atoms and is optionally substituted with $C_1$ to $C_4$ alkyl; $B^+$ is a quaternized nitrogen group selected from the group of A-D represented by the formulae:

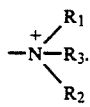   A wherein $R_1$, $R_2$ and $R_3$ are each independently selected from the group of alkyl, alkyleneoxidealkyl, alkyleneoxyalkenyl, alkylhydroxy, alkoxy, aryl, aralkyl, alkaryl, alkyleneamidoalkyl, alkylenecarbamoylalkyl, aryleneamidoalkyl and arylenecarbamoylalkyl radicals, said groups each having from 1 to 30 carbon atoms and at least one of $R_1$, $R_2$ and $R_3$ being a radical having from 8 to 30 carbon atoms;

   B wherein $R_4$ forms a double bond in a heterocyclic ring with the quaternized nitrogen or is the same as $R_1$, $R_2$ or $R_3$ in formula A and $R_5$ together with the quaternary nitrogen atom forms a 5 to 10 membered monocyclic ring, a 9 to 10 membered bicyclic ring or a 13 to 14 membered tricyclic ring, at least one of said rings containing from 1 to 2 hetero atoms selected from the group of nitrogen, sulfur and oxygen and being saturated or unsaturated as may occur for example in the rings of thiazirine, N-methyl-thiazine, N-methyl-oxazine, thiazepine, N-ethyl-oxazocine, diazocine, N-methylazonine, antipyrine, conyrine, coniine, collidine, diazine, imidazole, isoxazole, lutidine, N-methyl hexahydropyridine, morpholine, oxazole, picoline, piperidine, pyrine, pyrazole, pyridine, pyrrolidine, pyrrole, pyrroline, N-ethylbenzopyrrole, N,N'-dimethyl-dipyrrylmethane, decahydroquinoline, methyl indole, nicotine, quinoline, quinaldine, acridine and carbazole. As indicated, a heterocyclic ring of the $R_5$ moiety may contain carbonyl substitution or the ring itself can be substituted with a lower alkyl, amino or amido group.

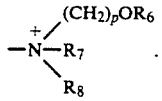   C wherein p is an integer having a value of from 2 to 4; $R_6$ is alkyl or alkenyl having from 1 to 30 carbon atoms; $R_7$ and $R_8$ are each independently selected from the groups of $-(CH_2)_pOR_1$, and a radical of $R_1$, $R_2$ or $R_3$ in formula A and at least one of $R_6$, $R_7$ and $R_8$ being a radical having from 8 to 30 carbon atoms; and

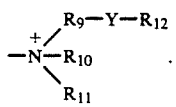   D wherein $R_9$ is alkylene having from 1 to 4 carbon atoms, phenyl or naphthyl optionally substituted with lower alkyl: Y is

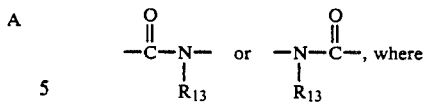

$R_{13}$ is hydrogen or lower alkyl; $R_{12}$ is alkyl of from 1 to 30 carbon atoms; $R_{10}$ and $R_{11}$ are each independently selected from the group of $-R_9-Y-R_{12}$ and a radical of $R_1$, $R_2$ or $R_3$ in formula A and at least one of $R_{12}$, $R_{10}$ and $R_{11}$ being radical having at least 8 carbon atoms.

The above nitrogen quaternized compounds and their preparations are described in detail in the above cited co-pending applications, which application teachings are incorporated herein by reference.

Sulfate and sulfonate reactant ion exchange agents which undergo ion exchange with the above halides include alkali metal and ammonium salts of the above sulfate and sulfonate anions and are defined by the formula

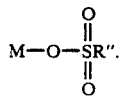   E wherein M is ammonium or an alkali or alkaline earth metal and R" is alkyl, alkoxy, aryl, aralkyl or alkaryl having from 1 to 20 carbon atoms optionally substituted with (1) to (20) units of ethyleneoxide and/or propyleneoxide or a $C_{12}$ to $C_{20}$ α-olefin or mixtures thereof.

Suitable species of this type include sodium methyl sulfate, sodium methyl sulfonate, lithium methyl sulfate, lithium methyl sulfonate, potassium ethyl sulfate, potassium ethyl sulfonate, (8)ethoxylated sodium methyl sulfate, (6)propoxylated sodium methyl sulfate, (10)propoxylated sodium ethyl sulfate, (4)ethoxylated potassium ethyl sulfonate, sodium lauryl sulfate, sodium lauryl sulfonate, potassium decyl sulfate, sodium dodecyl sulfonate, ammonium octadecyl sulfate, potassium octadecyl sulfonate, ammonium tetradecyl sulfate, sodium tetradecyl sulfonate, (4)ethoxylated lauryl sodium sulfonate, (4)ethoxylated lauryl sodium sulfate, sodium xylene sulfate, potassium xylene sulfonate, ammonium benzene sulfate, ammonium benzene sulfonate, ammonium ethylphenyl sulfate, sodium dodecylphenyl sulfonate, sodium toluene sulfate, sodium toluene sulfonate, sodium or ammonium $C_{12}$ to $C_{20}$ α-olefin sulfoantes, etc. Of these the sodium or ammonium methyl or ethyl sulfates and sulfonates and sodium or ammonium toluene sulfates and sulfonates are preferred.

The ion exchange reaction involving the present anion exchange agents and the aforementioned quaternized halides, preferalby the chlorides, can be effected directly when the anion of the anion exchange agent has a lower solubility than the halide, e.g. the chloride, of the quaternized halide compound. This method (Method 1) is carried out under mild conditions, for example between about room temperature and about 80° C. for a period of from about 10 minutes to about 4 hours, preferably between about 40° and about 65° C. for a period of from about 15 minutes to about 1 hour. The reactants are contacted in an aqueous solution in which the mole ratio of anion exchange agent to quaternized halide is between about 1:1 and about 1.5:1. The solid product which precipitates out of solution, is filtered and washed to remove alkali metal halide or ammonium halide by-product. Anion exchange agents having relatively low solubilities include sodium toluene sulfonate, sodium xylene sulfonate, etc.

The products of this invention can also be prepared by using an anion exchange resin (Method 2). In this case, the ion exchange is accomplished in a packed column with an ion exchange resin of the Amberlyte type which is a quaternized ammonium halide salt of a styrene-divinylbenzene copolymer having a macroreticular structure forming the matrix of said resin. An aqueous solution of the sulfate or sulfonate anion exchange agent is passed through the column to displace the halide and to replace the halide of the resin matrix with the corresponding sulfate or sulfonate anion. The quaternized halide is then passed through the column and exchanges its halide anion with the sulfate or sulfonate anion of the resin, thus regenerating the original ion exchange resin. This process is effected under ambient conditions with any of the alkali metal or ammonium sulfates or sulfonates described above.

The products of this invention can also be prepared by reactions involving a hydroxy alkyl lactam having the formula

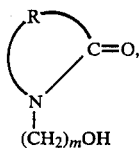

a tertiary amine and a suitable organo sulfonyl halide (Method 3).

In Method 3 the quaternized sulfonate salt of an alkyl lactam is formed in situ by reacting the hydroxy alkyl lactam with an organo sulfonyl halide in the presence of a tertiary amine having the formula

in a mole ratio of from about 1:2 to about 1:4 and an organo sulfonyl halide, preferably an organo sulfonyl chloride, e.g. ps
$$R''SO_2Cl \qquad\qquad F.$$

wherein R'' is as defined above and is preferably methyl or tolyl.

The mole ratio of lactam to sulfate or sulfonate is employed between about 1:1 and about 1:0.9.

This reaction is carried out in a suitable inert solvent such as a haloalkane or aromatic liquid, e.g. methylene chloride, benzene, toluene, xylene and the reaction is run at solvent reflux for a period of from about 15 minutes to about 4 hours. The mole ratio of solvent to reactants is between about 1:1 and about 4:1. In this reaction the sulfonate of the hydroxy alkyl lactam forms in situ and then reacts with the tertiary amine.

Finally, the present lactams can be prepared by Method 4 which comprises reacting the above hydroxyalkyl lactam with a secondary amine to produce the corresponding tertiary amine intermediate and then quaternizing the tertiary amine with sulfate or sulfonate of formula $$R''SO_2OR''' \qquad\qquad G.$$

wherein R'' is as defined above and R''' is a radical having from 1 to 20 carbon atoms, optionally substituted with (1) to (20) $C_2$ to $C_3$ alkyleneoxide units and is selected from the group of a $C_{12}$ to $C_{20}$ α-olefin or mixtures thereof, alkyl, aryl, alkaryl or aralkyl. Of these organo sulfates and sulfonates, those ethoxylated and non-alkoxylated compounds wherein R''' alkyl or tolyl and R'' is methyl, methoxy, ethyl, ethoxy, tolyl or tolyloxy are preferred.

The mole ratio of secondary amine having the formula

to lactam can vary between about 1:1 and about 1:2 and the mole ratio of lactam to quaternizing agent is about 1:1. This reaction is also conducted in the presence of an inert solvent such as those recited for Method 3 and is effected at a temperature above the melting point of the amine up to about 130° C. for a period of from about 1 to about 3 hours.

Most preferred quaternizing agents for the reactions involving the hydroxyalkyl lactams include dimethyl sulfate or sulfonate, diethyl sulfate, methyl toluene sulfate or sulfonate, octadecyl methane sulfonate, dodecylmethane sulfonate and lauryl (3)ethoxymethane sulfonate.

Specific preparations for the lactams which can be beneficially employed in this invention are provided in Examples 1–10 of copending U.S. patent application Ser. No. 188,522 now U.S. Pat. No. 4,885,158 and these examples are incorporated herein by reference.

The sulfate and sulfonate quaternized products of this invention show greatly increased heat stability with no product breakdown for the period tested, i.e. 1 month at 50° C. Accordingly, they are particularly suited for formulations normally stored for long periods or at elevated temperatures as encountered in warehouses, etc. They also impart antistatic and conditioning properties to the hair. The non-toxicity of the present lactams renders them ideally suitable as additives in cosmetic applications. Particular benefit is derived from their incorporation in shampoos, mouses and in clear conditioners. When employed in commercial formulations of the above type, they may be added to a concentration of between about 0.001 wt. % and about 30 wt. % based on total composition.

Having thus described the invention, reference is now had to the examples which illustrate preferred embodiments but which are not to be construed as limiting to the scope of the invention as more broadly described above and in the appended claims.

EXAMPLE I

Preparation of Dimethyl Stearyl-[N-(2-Pyrrolidonyl) Methyl] Ammonium Tosylate

To a glass chromatography column was charged 450 g. Amberlyte IRA 900 ion exchange resin*. The column was washed with one liter of methanol followed by one liter of distilled water.

* a macroreticular strongly anion exchange resin having a halide attached to the resin matrix of styrene/divinylbenzene A solution of sodium tosylate, prepared by addition of 332.9 g. p-toluene sulfonic acid monohydrate to 1720 g. water followed by neutralization with 140 g. of 50% sodium hydroxide, was then passed through the packed column at a rate sufficient to permit displacement of the Amberlyte halide and to replace it with toluene sulfonate. The column was then washed with one 1 liter of methanol. A solution of 153 g. of the product of dimethyl stearyl-[N-(2-pyrrolidonyl)methyl] ammonium chloride (98.4% pure) in 500 ml methanol was passed through the column at a rate sufficient to exchange the chloride anion with the toluene sulfonate of the resin. The column was then washed with 500 ml methanol and the methanol evaporated leaving 200 g. of 98% pure quaternized tosylate product. The product showed no loss of quaternary activity after storage at 50° C. for 60 days.

EXAMPLE II

Example I was repeated except that dimethyl stearamidopropyl[N-(2-pyrrolidonyl)methyl] ammonium chloride was substituted for dimethyl stearyl-[N-(2-pyrrolidonyl)methyl] ammonium chloride. The resulting dimethyl stearamidopropyl [N-(2-pyrrolidonyl)-methyl] ammonium tosylate quaternized product was obtained in 98% yield.

EXAMPLE III

Example I was repeated except that methyl dihexadecyl-[N-(2-pyrrolidonyl)methyl] ammonium chloride was substituted for dimethyl stearyl-[N-(2-pyrrolidonyl) methyl] ammonium chloride. The resulting quaternized product, methyl dihexadecyl [N-(2-pyrrolidonyl)-methyl] ammonium tosylate was recovered in 98% yield.

EXAMPLE IV

Example I was repeated except that dimethyl phenylene amido butyl [N-(2-pyrrolidonyl)methyl] ammonium chloride was substituted for dimethyl stearyl [N-(2-pyrrolidonyl)methyl] ammonium chloride. The resulting quaternized product, dimethyl phenylene amido butyl [N-(2-pyrrolidonyl)methyl] ammonium tosylate was recovered in 98% yield.

EXAMPLE V

Example I was repeated except that methyl-pyrrolidonyl [N-(2-pyrrolidonyl)methyl] ammonium chloride is substituted for dimethyl stearyl [N-(2-pyrrolidonyl)methyl] ammonium chloride. The quaternized product methyl-pyrrolidonyl [N-(2-pyrrolidonyl) methyl] ammonium tosylate is obtained in greater than 80% yield.

EXAMPLE VI

Curl Retention*

*Curl retention is a quantitative measure of hold in hair fixatives such as hair sprays, mousses, glazes, gels and in reactive hair processing solutions such as permanent waving solutions.

Dimethyl stearyl [N-(2-pyrrolidonyl)methyl] ammonium tosylate (A) was compared to dimethyl stearyl [N-2-pyrrolidonyl)methyl] ammonium chloride (B) in the following hair set formulations.

| Curl Retention* Dimethyl stearyl [N-(2-pyrrolidonyl)methyl] ammonium tosylate (A) was compared to dimethyl stearyl [N-(2-pyrrolidonyl)methyl] ammonium chloride (B) in the following hair set formulations. | | |
|---|---|---|
| Ingredient | % By Weight | |
| Ethanol, (SD-40-2) | 66.00 | 66.00 |
| Vinylcaprolactam/PVP/Dimethyl-aminoethyl Methacrylate Copolymer (Gaffix VC-713) | 12.00 | 12.00 |
| Deionized Water | 20.00 | 20.00 |
| Compound A | 2.00 | — |
| Compound B | — | 2.00 |
| | 100.00 | 100.00 |

*Curl retention is a quantitative measure of hold in hair fixatives such as hair sprays, mousses, glazes, gels and in reactive hair processing solutions such as permanent waving solutions.

A hair sample from a tress of light brown, good condition, medium fine hair was moistened with the above solution containing 2% of Compound A. Another sample from the same tress was moistened with the above solution containing 2% of Compound B.

In both cases the hair was rolled on 0.5" rollers, dried and combed out. The hair curl retention in each test was determined as follows.

TABLE 1

| Time in Humidity Chamber | Formulations | |
|---|---|---|
| (90% humidity at 80° F.) | contg 2% A | contg 2% B |
| 15 min. | 48.4% | 32.5% |
| 30 min. | 33.1% | 14.1% |
| 45 min. | 28.4% | 12.5% |
| 60 min. | 26.4% | 12.1% |
| 75 min. | 24.0% | 11.3% |

EXAMPLE VII

Shampoo Conditioning Effects

Compounds A and B were also compared for conditioning effects using the following formulations on a tress sample of light brown, medium fine hair of poor texture due to dryness and splitting, following permanent waving.

| SHAMPOO FORMULAE | | | |
|---|---|---|---|
| | % By Weight | | |
| Ingredient | Shampoo x | Shampoo y | Shampoo z |
| Deionized Water | 58.90 | 58.90 | 60.90 |
| Ammonium Lauryl Sulfate (Standapol AHV) | 35.00 | 35.00 | 35.00 |
| Cocamidopropyl Betaine (Monatine CAB) | 4.00 | 4.00 | 4.00 |
| Compound A | — | 2.00 | — |
| Compound B | 2.00 | — | — |
| Kaltron CG (Rohm & Haas) | 0.10 | 0.10 | 0.10 |
| Citric Acid, 50% Aqueous | To pH 4.5 | To pH 4.5 | To pH 4.5 |
| | 100.00 | 100.00 | 100.00 |

The hair was shampooed for 2 minutes and inspected by Scanning Electron Microscopy (SEM), according to the following procedure.

A tress sample of virgin hair was subjected to an alkaline cold permanent wave and the cuticle layer was intentionally damaged by extended exposure to the processing solution (10-12 minutes). The tress sample was divided into 3 groups. Each tress was shampooed 3 times with Breck shampoo and rinsed under tepid tap water for 3 minutes and then soaked in ethanol for 15 minutes to remove any remaining surfactants. The tresses were allowed to air dry overnight, after which they were treated as follows:

Sample Tress 1

This tress was shampooed 3 times with shampoo composition x containing 2% of the quaternized lactam tosylate (A), then rinsed for 3 minutes with tepid tap water and allowed to air dry overnight. Photomicrographs of a hair fiber from this sample were taken at 5000×, 6000× and 1000× magnification.

Sample Tress 2

Same procedure as for sample tress 1 was repeated except that shampoo composition y was substituted for x.

Sample Tress 3 (Control)

Same procedure as for sample tress 1 was repeated except that quaternized additives A and B were omitted and composition z was substituted.

Examination of the photomicrographs showed that the cuticle layer in sample tress 1 was effectively coated. The reamining sample tresses 2 and 3 failed to produce a coating and were similar in appearance.

Overlapping cuticle of the hair shaft treated with composition x was smoothed, thus providing significantly improved combability and forming a protective shield over the hair shaft. No difference was noted in the hair cuticle treated with composition y and z.

EXAMPLE VIII

An evaluation of the quaternized lactam, dimethyl stearyl-[N-(2- pyrrolidonyl)methyl] ammonium tosylate additive in a standard type of hair bleach (Helene Curtis White Frosting Bleach) was made as described below.

Each of the representative compositions X and Y comprising the hair bleach formulation were divided into equal portions. The first divided portions of X-Y were combined and immediately applied to portions of the hair selected for frosting on the left side of the scalp of the subject undergoing testing. The subject had (brown) hair of good texture and quality. To the remaining divided X-Y portions, after being combined, 1 wt. % of the quaternized dimethyl stearyl-[N-(2-pyrrolidonyl)methyl] ammonium tosylate was added. The later mixture of combined X-Y portions, containing the quaternized lactam, was applied to equal portions of the hair selected for frosting on the right side of the scalp of said subject.

| | Wt. % |
|---|---|
| X. Ingredients in Bleach | |
| Polyoxyethylene glycol oleyl ether | 14.02 |
| Citric acid | 7.01 |
| Ethyl alcohol | 4.67 |
| Monoethanol amine | 2.80 |
| Ethoxylated nonyl phenol | 2.33 |
| $H_2O_2$ (50%) | 6.89 |
| Potassium persulfate | 2.95 |
| Ammonium persulfate | 0.92 |
| Sodium persulfate | 2.95 |
| Disodium ethylenediamine tetra acetic acid | 0.13 |
| Sodium metasilicate | 6.15 |
| Deionized distilled water | 49.18 |
| Y. Developer | |
| $H_2O_2$ (30%) | 20.00 |
| Nonoxynol-9 | 5.00 |

-continued

| | Wt. % |
|---|---|
| Nonoxynol-4 | 2.00 |
| Phosphoric acid | 0.50 |
| Cetyl alcohol | 0.50 |
| Stearyl alcohol | 0.50 |
| Water | 71.50 |

The combined lotions on each side of the scalp were separately maintained on the hair for the prescribed period, 30 minutes, after which the lotions were rinsed away with water. The hair was blown dry and the following evaluations comparing the hair on the right and left side of the scalp were made. The results are reported in Table II.

TABLE II

| | Left Side | Right Side |
|---|---|---|
| BLEACHING PROCESS | | |
| Ease of Application | good | excellent |
| Processing Time | 30 min. | 30 min. |
| Scalp and Skin Irritation | none | none |
| Ease of Rinse-Out | good | good |
| WET EVALUATION OF HAIR | | |
| Feel | fair | excellent |
| Dryness | slight dryness | completely conditioned |
| Combability | fair | excellent |
| Manageability | good | excellent |
| Snarling | some | none |
| Porosity | slight | none |
| DRY EVALUATION OF HAIR | | |
| Combability | fair | excellent |
| Snarling | some | none |
| Degree of Bleach | yellow | very pale yellow |
| Breakage | none | none |
| Softness | good | excellent |
| Body | good | excellent |
| Manageability | good | excellent |
| Conditioning | smooth | very smooth |
| Luster | good | excellent |
| HAIR CONDITION AFTER 3 WEEKS | | |
| Color | yellow | very pale yellow |
| Blending (on hair shaft) | fair | excellent |
| Coverage at ends | fair | excellent |
| Lifting of color (pigmented hair) | good | excellent |
| Color Retention | good | excellent |
| Fading | some | very little |
| Skin and Scalp Irritation | none | none |

EXAMPLE IX

The quaternized lactam, dimethyl stearyl-[N-(2-pyrrolidonyl)methyl] ammonium tosylate was also evaluated as an additive to a standard hair dye formulation namely (Loving Care—Medium Brown). Each of the representative compositions A, B and C comprising the hair dye formulation were divided in equal portions. The first divided portions A-C were combined and immediately applied to the left side of the hair on the scalp of the subject undergoing testing. The subject had dark brown and grey hair of fine texture and quality. To the remaining divided portions A-C, after being combined, 1 wt. % of the quaternized dimethyl stearyl-[N-(2-pyrrolidonyl)methyl] ammonium tosylate was added. The later combined A-C portion, containing the organic quaternized lactam, was applied to the hair on the right side of the scalp of said subject.

| | Wt. % |
|---|---|
| A. Ingredients for Color | |
| Water | qs |
| Tall oil acid | 7.50 |
| Propylene glycol | 4.40 |
| Iso $C_3$ alcohol | 4.35 |
| Octoxynol-1 | 3.50 |
| Nonoxynol-4 | 2.00 |
| $NH_4OH$, 26° Baume | 1.15 |
| Ethoxydiglycol | 0.75 |
| Cocamide diethanolamide | 3.50 |
| Polyethyleneglycol-8 tallow amine | 0.50 |
| Sulfated Castor Oil | 1.50 |
| Erythorbic Acid | 0.50 |
| Ethylenediaminetetraacetic acid | 0.01 |
| Glycol | 0.25 |
| Na sulfite | 0.05 |
| N,N-bis(2-hydroxyethyl)-p-phenylenediamine sulfate | 0.18 |
| 1-Naphthol | 0.08 |
| Resorcinol | 0.31 |
| p-Phenylenediamine | 0.35 |
| Fragrance | 0.50 |
| Adjust pH to 9.8 | |
| B. Ingredients for Developer | |
| $H_2O_2$, 30% | 20.00 |
| Nonoxynol-9 | 5.00 |
| Nonoxynol-4 | 2.00 |
| Phosphoric Acid | 0.50 |
| Cetyl Alcohol | 0.50 |
| Stearyl Alcohol | 0.50 |
| Water | 71.50 |
| C. Ingredients in Conditioner Lotion | |
| Hydroxyethyl Cellulose | 1.00 |
| Ethoxydiglycol | 0.50 |
| Polyquaternium - 6 | 0.50 |
| Cocoamphocarboxypropionate | 25.00 |
| Cocamidopropyl Betaine | 10.00 |
| Glycol | 5.00 |
| Quaternium - 15 | 0.25 |
| Sorbic Acid | 0.20 |
| Phosphoric Acid | to pH 3.0 |
| Fragrance | 0.20 |
| Water | qs |

The lotions on the hair on each side of the scalp were allowed to remain for a period of 30 minutes, after which they were rinsed away with water. The hair was then shampooed and blown dry. The following evaluations comparing the hair on the right and left side of the scalp were made. The results of this evaluation are reported in Table III.

TABLE III

| | Left Side | Right Side |
|---|---|---|
| HAIR COLORING PROCESS | | |
| Ease of Application | good | excellent |
| Processing Time | 30 min. | 30 min. |
| Skin and Scalp Irritation | none | none |
| Penetration | good | excellent |
| Ease of Rinse-Out | good | good |
| WET EVALUATION OF HAIR | | |
| Feel | fair | slippery |
| Dryness | dry | fully conditioned |
| Combability | fair | excellent |
| Manageability | fair | excellent |
| Snarling | slight | none |
| Porosity | slight | none - hair coated |
| DRY EVALUATION OF HAIR | | |
| Combability | fair | excellent |
| Snarling | some | none |
| Coverage of grey | good | excellent |
| Overall coverage | good | excellent |
| Softness | fair | very soft |
| Body | fair | excellent |
| Manageability | fair | excellent |
| Conditioning | little | extremely good |
| Luster | fair | excellent |
| HAIR CONDITION AFTER 3 WEEKS | | |
| Tone at Roots | darker grey showing | somewhat darker - grey still covered |
| Blending on Shaft | fair | good |
| Coverage at ends | good | excellent |
| Lifting of color (pigmented hair) | good | excellent |
| Color Retention (overall) | good | excellent |
| Fading (overall) | some | none |
| Skin and Scalp Irritation | none | none |

EXAMPLE X

A reducing lotion for a conditioned permanent waving preparation was made according to the following formulation Parts A and B.

| Reducing Lotion | |
|---|---|
| Ingredients | Wt. % |
| Part A | |
| tosylate of Example II | 2.00 |
| emulsifying wax | 2.00 |
| deionized water | 80.40 |
| phenoxyphthanol (preservative) | qs |
| fragrance | qs |
| Part B | |
| ammonium thioglycolate (60%) | 11.70 |
| ammonium hydroxide (28%) | 3.90 |
| | 100.00 |

The emulsifying wax was melted and water at 80° C. was added with continuous high shear mixing after which the tosylate was added with stirring until the mixture cooled to 50° C. A small amount of fragrance and preservative about 0.3%, was then mixed into the composition.

In a separate vessel, ammonium hydroxide was added to the thioglycolate and the resulting mixture slowly added with constant stirring to the cream preparation of part A. The pH of the resulting mixture was then adjusted to 9.2–9.3. This cream mixture was then applied to a test subject having normal brown hair of medium texture and good condition according to the following procedure.

The test subject hair was saturated with water, allowed to drip dry, after which the hair was partitioned into 25 sections and the distal ends of each section wrapped in a porous end paper and roled on a permanent hair setting rod. To the remaining scalp portion was applied a reducing lotion of the above formulation except that 2% ethoxylated nonylphenol surfactant was substituted for the tosylate. The reducing lotions were allowed to remain on the hair for a period of 8 minutes at room temperature, after which the rolled hair was thoroughly rinsed with water, allowed to drip dry and a neutralizing lotion was then uniformly applied to saturate the hair. The neutralizing solution had the following formulation.

| Components | % by Weight |
|---|---|
| Hydrogen peroxide | 4.50 |

| Components | % by Weight |
| --- | --- |
| Citric acid | 0.20 |
| Polyoxyethylene lauryl ether | 0.50 |
| Latex opacifier | 0.10 |
| Phenacetin | 0.04 |
| Deionized water | 94.26 |
| Fragrance | 0.40 |

The neutralizer was allowed to remain on the hair for 3 minutes, after which the hair was rinsed and the rods removed. The hair was again rinsed and brush dried.

The half section of the head treated with the reducing lotion containing the present lactam possessed excellent wet and dry combability, and the hair had a silky soft texture characteristic of conditioning which surpassed that witnessed with other commercial waving lotions. The remaining half section of the hair to which the reducing lotion containing no lactam was applied, showed noticeably less combability and softness and less curl.

The coatability of the present formulation containing organic quaternized lactam also reduces, to a marked extent, the hair damage attributed to peroxides and this coating property is responsible for significant improvements in altering the structure of hair having a kinky quality.

The present lactams have significantly lower melting points than their quaternized halide salt counterparts and are more thermally stable; thus, they are more readily incorporated in formulations. These quaternized organic salt lactams, although non-polymeric in nature, nevertheless possess excellent hair coating properties, a property essential for combability. The present products, being oil soluble, are particularly adapted to the conditioning of ethnic hair, thereby providing texture softening and snarl resistance. Being non-polymeric and having a single cationic site, these quaternized organic salts are more easily removed during shampooing. A high degree of set curl retention is also noted under conditions of high humidity which property is lacking in water soluble quaternized lactam salts.

What is claimed is:

1. A hair treating composition containing an inert carrier, an active hair processing agent selected from the group consisting of hair bleaching agent, a hair coloring agent, a hair setting agent, a hair reducing agent employed to alter hair structure and an oxidizing agent employed to arrest the reducing action of a reducing agent used in the structural alteration of hair and an effective conditioning amount of an organic quaternized lactam having the formula

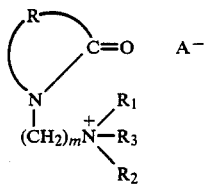

wherein m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkyleneoxyalkyl, alkyleneoxyalkenyl, alkoxy, hydroxyalkyl, aryl, aralkyl, alkaryl, alkyleneamidoalkyl, alkylenecarbamoylalkyl, aryleneamidoalkyl and arylenecarbamoylalkyl radicals, and $R_2$ and $R_3$, together with the quaternized nitrogen atom can form a 5 to 14 membered heterocyclic radical containing from 1 to 2 heteroatoms selected from the group of nitrogen, sulfur and oxygen, in which case $R_1$ can represent a double bond in the heterocyclic structure or can be any of the aforementioned groups for $R_1$, $R_2$ and $R_3$; said groups $R_1$, $R_2$ and $R_3$ each having up to 30 carbon atoms and at least one of $R_1$, $R_2$ and $R_3$ being a radical having from 8 to 30 carbon atoms when $R_2$ and $R_3$ are not part of a heterocyclic moiety; and $A^-$ is an anion derived from an oxylated sulfur compound, having the formula:

$$R'SO_3^-$$

wherein R' is alkyl, alkoxy, phenyl, phenoxy, alkylenephenyl, alkylenephenoxy, phenylenealkyl or phenyleneoxyalkyl and wherein the alkyl moieties of said R' groups contain from 1 to 20 carbon atoms and said R' groups are optionally alkoxylated with from 1 to 20 units of ethyleneoxide and/or propylene oxide.

2. The composition of claim 1 wherein said hair processing agent is a hair reducing agent employed to alter hair structure.

3. The composition of claim 1 wherein said hair processing agent is an oxidizing solution employed to arrest the reducing action of a reducing agent in the structure alteration of hair.

4. The composition of claim 1 wherein said hair processing agent is a hair bleaching agent.

5. The composition of claim 1 wherein said hair processing agent is a hair color altering agent.

6. The composition of claim 1 wherein said composition is a shampoo.

7. The composition of claim 1 wherein said hair processing agent is a hair setting agent.

8. The composition of claim 1 wherein said organic quaternized lactam represents between about 0.001 and about 30 weight % based on total composition.

9. The composition of claim 8 wherein said organic quaternized lactam represents between about 0.01 and about 7 weight % based on total composition.

10. The composition of claim 1 wherein said lactam is a pyrrolidone.

11. The composition of claim 10 wherein said lactam has the formula

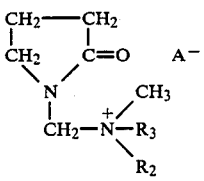

wherein $A^-$, $R_2$ and $R_3$ are as defined.

12. The composition of claim 1 wherein said organic quaternized lactam $R_1$ is lower alkyl, at least one of $R_2$ and $R_3$ is $C_{12}$ to $C_{18}$ alkyl or a hydrogenated tallow or coco radical.

13. The composition of claim 12 wherein $A^-$ is tosyl.

14. The composition of claim 12 wherein said organic quaternized lactam represents between about 0.75 and about 5 weight % of the total composition.

* * * * *